United States Patent [19]

Haigwood

[11] Patent Number: 5,108,909
[45] Date of Patent: Apr. 28, 1992

[54] EXPRESSION OF TPA IN MAMMALIAN CELLS

[75] Inventor: Nancy L. Haigwood, Oakland, Calif.

[73] Assignee: Chiron Corporation, Emeryville, Calif.

[21] Appl. No.: 97,271

[22] Filed: Sep. 17, 1987

Related U.S. Application Data

[63] Continuation of Ser. No. 715,237, Mar. 22, 1985, abandoned.

[51] Int. Cl.$^5$ .................. C12P 21/02; C12N 15/12; C12N 15/85
[52] U.S. Cl. .................. 435/69.2; 435/172.3; 435/241.2; 435/320.1; 536/27; 935/34; 935/61
[58] Field of Search .................. 435/212, 226, 172.3, 435/240.2, 235, 69.1, 69.2, 69.6, 71.1, 91, 172.1, 240.1, 320, 320.18; 935/14, 22, 24, 32, 39, 70, 10, 11, 34, 61, 71; 536/27

[56] References Cited

U.S. PATENT DOCUMENTS

| | | | |
|---|---|---|---|
| 4,751,084 | 6/1988 | Feder et al. | 424/94.64 |
| 4,753,879 | 6/1988 | Rosa et al. | 435/172.3 |

FOREIGN PATENT DOCUMENTS

| | | | |
|---|---|---|---|
| 0108667 | 5/1984 | European Pat. Off. | 435/172.3 |
| 0173552 | 3/1986 | European Pat. Off. | |
| 0211260 | 2/1987 | European Pat. Off. | |
| 0234051 | 9/1987 | European Pat. Off. | |
| 0253241 | 1/1988 | European Pat. Off. | 435/172.3 |
| 0253582 | 1/1988 | European Pat. Off. | |
| 0269382 | 6/1988 | European Pat. Off. | |
| 0275606 | 7/1988 | European Pat. Off. | 435/172.3 |
| 0287187 | 10/1988 | European Pat. Off. | |
| 0290118 | 11/1988 | European Pat. Off. | |
| 2189249 | 10/1987 | United Kingdom. | |
| 8704722 | 8/1987 | World Int. Prop. O. | 435/172.3 |
| 8705954 | 10/1987 | World Int. Prop. O. | 435/172.3 |

OTHER PUBLICATIONS

Gillies, S. et al., Cell, vol. 33, pp. 717-728, 1983.
Ny, T. et al., Proc. Natl Acad Sci, vol. 81, pp. 5355-5359, 1984.
Kaufman, R. et al., Molec and Cell Biology, vol. 2, No. 11, pp. 1304-1319 (1982).
Kaufman, R. et al., Molec. and Cell Biology, vol. 5, No. 7, pp. 1750-1759 (1985).
Pennica, D. et al., Nature, vol. 301, pp. 214-221 (1983).
Craik, C. et al., Science, vol. 220, pp. 1125-1129 (1983).
Breathnach, R. et al., Oralbumin gene: Evidence for a leader sequence in mRNA and DNA sequences . . . , vol. 75, PNAS, 4853-4857 (1978).
Sharp, P. A., Speculations on RNA Splicing, Cell 23, 643-646 (1981).
Chu, G. et al. A gene chimaera of SV40 and mouse B-globin is transcribed and properly spliced, Nature 289, 378-382 (1981).
Khoury, G. et al., New Chimeric Splice Junction in Adenovirus Type 2-Simian Virus 40 Hybrid Viral mRNA, J. of Virology, 36, 143-151 (1980).
Pamela Mellon et al., Cell, vol. 27, pp. 279-288 (1981).
Nava Sarver et al., Molecular and Cellular Biology, vol. 1, pp. 486-496 (1981).
Michael Karin et al., Proc. Natl. Acad. Sci. U.S.A., vol. 80, pp. 4040-4044 (1983).
Monika Lusky et al., Cell, vol. 36, pp. 391-401 (1984).
Michael Wigler et al., Proc. Natl. Acad. Sci. U.S.A., vol. 76, pp. 1373-1376 (1979).
Michael Wigler et al., Cell, vol. 16, pp. 777-785 (1979).
B. Wold et al., Proc. Natl. Acad. Sci. U.S.A., vol. 76, pp. 5684-5688 (1979).
Randal J. Kaufman et al., Molecular and Cellular Biology, vol. 2, pp. 1304-1319 (1982).
Randal J. Kaufman et al., Molecular and Cellular Biology, vol. 5, pp. 1750-1759 (1985).

Primary Examiner—James Martinell
Attorney, Agent, or Firm—Spencer & Frank

[57] ABSTRACT

Improved expression of tPA in mammalian cells is achieved employing a promoter region functional in a mammalian cell with a DNA sequence coding for tPA, where the sequence is interrupted by at least one intron. Particularly, a viral promoter is employed in conjunction with a hybrid gene having portions of the coding sequence uninterrupted by introns as compared to the wild-type gene and coding sequences interrupted by introns or the wild-type gene or mutants thereof.

Plasmid pSV7tPA2I was deposited on Feb. 14, 1985 and given A.T.C.C. Accession No. 40163.

15 Claims, 1 Drawing Sheet

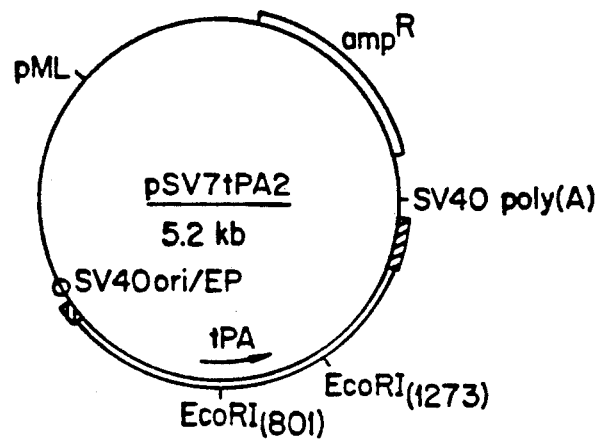
FIG. 1a
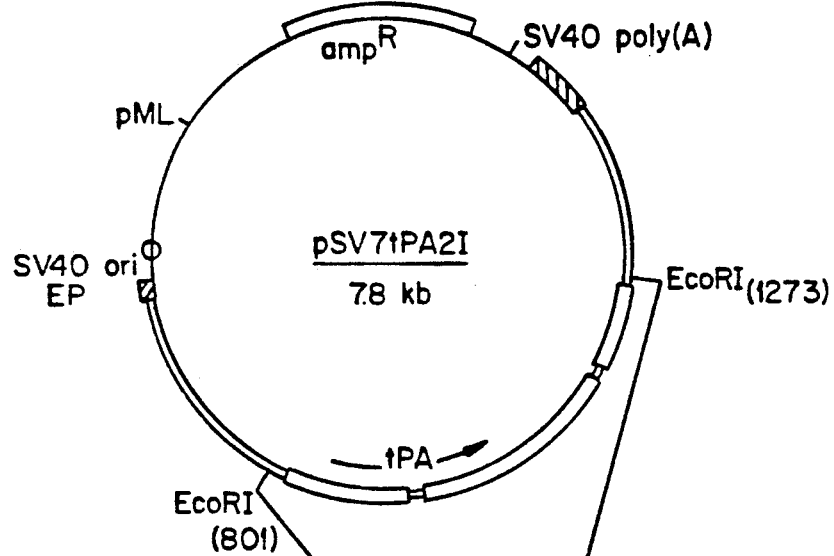
FIG. 1b
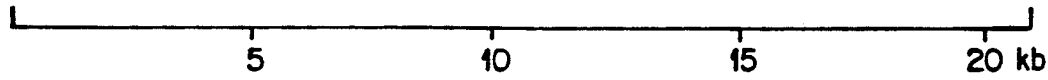

his application is a continuation of application Ser. No. 06/715,237, filed Mar. 22, 1985 now abandoned.

EXPRESSION OF TPA IN MAMMALIAN CELLS

This application is a continuation of application Ser. No. 06/715,237, filed Mar. 22, 1985 now abandoned.

BACKGROUND OF THE INVENTION

1. Field of the Invention

There is an increasing number of genes being introduced into foreign hosts for expression. A substantial proportion of the genes which are employed are obtained from cDNA. In those instances where the natural gene has one or more introns, it has frequently been found to be much more convenient to employ the cDNA rather than handling larger pieces of DNA which involve the intron and add further complexity to the manipulation of the gene in conjunction with the regulatory signals associated with expression and replication.

The function of introns is still not well established. While much progress has been made in an understanding of the splicing mechanism involved in removing the introns, the role of introns in the process of transcription and translation has not been explained. The fact that cDNA can be readily expressed establishes that introns are not essential for the expression of a coding sequence.

An important factor in the preparation and production of polypeptides and proteins in cellular hosts is the efficiency with which the polypeptide or protein is produced. Since nutrients must be supplied to the host to maintain its viability, the nutrients are used primarily for the growth and replication of the host, rather than the product of interest. It thus becomes important to maximize utilization of the nutrients for the production of the desired product, as well as enhancing the proportionate amount of the desired product as compared to the total protein produced, which greatly aids in the efficiency with which the desired product may be isolated in pure form.

2. Description of the Prior Art

Pennica et al., *Nature* (1983) 301:21-221; UK Patent Appln. No. GB 2,119,804 describe the isolation and cloning of a cDNA for human tissue plasminogen activator. Ny et al., *Proc. Nat'l Acad. Sci. USA* (1984) 81:5355-5359 describe the human tissue-type plasminogen activator gene and the exon-intron relationship. Hamer and Leder, *Cell* (1979) 18:1299-1302, suggest that introns aid in the stability of RNA, while Gething and Sambrook, "The Expression of the Influenza Virus Hemagglutinin Gene from SV-40-HA Recombinants" in Eukaryotic Viral Vectors, ed., Y. Gluzman, pp. 29-33 (1982), indicate the opposite experience. Kaufman and Sharp, *Molec. and Cell Biol.* (1982) 2: 1304-1319 show that a hybrid intron can be used in the expression of dihydrofolate reductase cDNA. Lau and Kan, *Proc. Nat'l Acad. Sci. USA* (1983) 80:5225-5229, describe cosmid vectors and their use in COS cells and permanent cell lines.

SUMMARY OF THE INVENTION

Improved expression of tissue plasminogen activator is obtained in mammalian cells by employing a coding sequence for tissue plasminogen activator (tPA) which is interrupted by at least one intron. Either the wild-type tissue plasminogen activator gene or a chimeric gene is employed which codes for the desired protein product. Active promoters are employed which result in enhanced yields of tissue plasminogen activator.

BRIEF DESCRIPTION OF THE DRAWING

FIG. 1a and FIG. 1b depict two related plasmids, one being an embodiment of the subject invention.

FIG. 1a shows a schematic diagram of the tPA cDNA expression plasmid pSV7tPA2. Hatched regions indicate 5' and 3' untranslated sequences and small white curvilinear regions indicate the coding sequences for preprotPA. The SV40 origin is noted as a circle, and the approximate locations of the SV40 early promoter (EP) and early region polyadenylation sequences (poly(A)) are noted. The EcoRI sites at positions 801 and 1273 are also indicated.

Below this plasmid is FIG. 1b showing the plasmid bearing the chimeric tPA gene, pSV7tPA2I. As above, small white curvilinear regions indicate coding sequences, interrupted by introns (large white boxed regions) from the genomic tPA gene.

A schematic diagram of the genomic tPA gene is drawn at the bottom of FIG. 1b to indicate the region excised from the genomic clone to replace the cDNA between positions 801 and 1273. Restriction sites for EcoRI (E), BamHI (B) and NruI (N) are marked on the genomic map.

DESCRIPTION OF THE SPECIFIC EMBODIMENTS

DNA Constructions and their use for improved expression of tissue plasminogen activator (tPA) are provided where the DNA constructions include a coding sequence for mammalian tissue plasminogen activator, where the coding sequence is interrupted by at least one intron. The genomic gene or chimeric gene lacking one or more of the naturally-occurring introns is joined to transcriptional regulatory sequences functional in the mammalian host.

The gene which is employed for encoding the tissue plasminogen activator may encode for mature tissue plasminogen activator, a precursor or proform of tissue plasminogen activator, which intends the loss of an N-terminal sequence, or a pre-proform involving a leader sequence which provides for secretion.

The tPA coding sequence which is employed will be characterized by having at least one intron of at least about 100 bp, more usually at least about 300 bp, and not more than about 5 kbp, usually not more than about 4 kbp. The introns which are employed may be the naturally-occurring introns associated with the tissue plasminogen activator gene or introns derived from a different mammalian gene, such as beta-globin, or hybrid introns such as the adenovirus-immunoglobulin hybrid intron used to express a dhfr cDNA as described by Kaufman and Sharp, supra.

Desirably, native introns are employed and at their native site. The gene will usually have fewer than the natural number of introns, the gene may have from 1 to 13 introns, usually 2 to 13 introns, preferably from 2 to 6 introns or from 9 to 13 introns, particularly among the introns "F" to "M", using the designations of Ny et al., supra, which disclosure is incorporated herein by reference. The DNA fragment encoding the human tissue plasminogen activator gene and including the introns will be at least about 2.5 kbp and not more than about 30 kbp. The introns will have the appropriate splicing signals at their termini.

A large number of different promoter regions mag be employed which are active in mammalian cells. Heterologous promoters may be obtained from mammalian viruses, such as SV40 (early or late) adenovirus (early or late) or retroviruses (LTRs). Alternatively, regulatable promoters such as those from mouse or human metallothioneins I and II, heat shock proteins, etc. may be employed. Descriptions of these promoters may be found in Hamer et al. (1983) in Eukaryotic Viral Vectors, Y. Gluzman ed. pp 7-12, Mayo et al., *Cell* (1982) 29:99-108 and Karin et al., *Nature* (1984) 308:513-519.

Any convenient polyadenylation site may be used, such as one associated with the promoter region, native to the tissue plasminogen activator gene, or from another mammalian gene.

Of particular interest is the combination of the SV-40 enhancer and early promoter region, as well as replication system, but lacking the T-antigen, in combination with COS cells, which contain the T-antigen.

The tissue plasminogen activator gene may be obtained from any mammalian host, particularly primate (e.g., human), bovine, equine, canine, porcine, feline, rodentia, or the like.

Once an expression cassette has been prepared containing the 5' and 3' untranslated regions containing transcriptional and translational initiation and termination regulatory sequences usually flanking the intron-containing gene, the cassette may then be joined to a vector for transformation into a mammalian cell host. In some instances transcriptional regulatory regions, e.g., enhancers, may be included in an intron.

The particular order in which the parts are brought together is not a critical element of the subject invention, so that the flanking regions might be first bound to a replication system including a marker or other regions, such as enhancers, transcriptional regulatory regions, or the like, prior to insertion of the gene. The manner in which the various fragments are brought together will depend on a number of factors related to ease of construction, choice of restriction sites, availability of particular fragments, and the like.

In part, the choice of replication system will depend upon whether one wishes to obtain transient or stable expression. For transient expression, episomal elements based on viral sequences (e.g., SV-40), containing an origin of replication are used. Stable expression can be achieved using episomal elements (e.g., bovine papilloma virus based vectors) or sequences integrated into the genome.

A number of these viral sequences have been joined to markers, such as the genes gpt, neo and dhfr. These markers allow for selection of cells containing the vector and for amplification of the integrated foreign sequences. If desired, to further enhance the production of the tissue plasminogen activator, one may amplify the gene by preparing a tandem construct where the tissue plasminogen activator cassette is in tandem with an expression cassette of a gene such as dhfr, metallothionein, or the like. Alternatively, cells may be cotransformed with one construct containing the tPA expression cassette and a second independent construct containing the selectable marker.

The host may be any convenient mammalian cell which is capable of splicing and expressing the tissue plasminogen activator efficiently in culture. A wide variety of cells exist such as CHO cells, COS cells, LTK cells, HeLa, and CV-1. These cells are merely set forth as illustrative of well-established cell lines, and are not intended to limit the subject invention to any particular established cell line, but other cell lines presently established or established in the future may be advantageously employed.

The genomic tissue plasminogen activator gene may be obtained as described by Ny et al., supra, and the cDNA gene may be obtained as described by Pennica, supra, or in UK Patent Application No. 2,119,804. These sequences may then be used in a variety of ways. The entire gene may be used and inserted into an expression vector having the appropriate regulatory sequences to provide the expression cassette Joined to a replication system or DNA which will aid integration into the host genome or both. Alternatively, based on the restriction maps provided by Ny et al., supra, and Pennica et al., supra, various fragments may be obtained from the cDNA and genomic DNA gene sequences and joined together to provide hybrid genes, where a portion is from the cDNA gene and a portion from the genomic gene. The hybrid gene may be prepared by the substitution of a portion of the genomic gene with a cDNA fragment, or vice versa, where the hybrid gene terminates with either the cDNA or the genomic DNA or the 5'-proximal portion of one of the tissue plasminogen activator genes is joined to the 3'-proximal portion of the other gene.

The expression cassette may be introduced into the host by any convenient means, such as calcium-phosphate-precipitated DNA, transfection, transduction, or the like. The particular manner is not critical to this invention, and once the DNA has been introduced into the host cell, the procedure need not be repeated. Therefore, while high efficiencies of introduction of the expression cassette into the host is desirable, it is not necessary.

The mammalian cells may then be grown in an appropriate medium, Such as DulbeccO's Modified Eagle Medium (DMEM) containing 10% to 20% fetal calf serum or other medium in which these cells may be stably maintained. Depending upon whether the leader sequence has been retained and the product is capable of secretion, where the product is produced extracellularly, the medium may be continuously or repetitively exchanged and the tissue plasminogen activator protein or proform isolated from the medium. Where the leader is not retained and the tissue plasminogen activator is maintained intracellularly, the cells may be harvested, killed and lysed, and the tissue plasminogen activator isolated.

Various techniques for isolation and purification are known, such as affinity chromatography, HPLC, reverse phase HPLC, electrophoresis, extraction, gel permeation chromatography, and the like. By employing the expression constructs of the subject invention, the yields of tissue plasminogen activator can be substantially enhanced as compared to employing the cDNA gene, which has been previously employed both in prokaryotic and eukaryotic cells.

The following examples are offered by way of illustration and not by way of limitation.

EXPERIMENTAL

1. Construction of Expression Vectors Containing a tPA Hybrid Gene

A human genomic DNA library consisting of a HaeIII partial digest of human DNA cloned into bacteriophage lambda Charon 4A at the EcoRI sites (available from T. Maniatis) was screened with a tPA cDNA clone 23 which comprises approximately bases 1270 to 2540 of the cDNA sequence as numbered by Pennica et al. supra. Approximately one million plaques were screened, yielding 12 clones which were positive for tPA sequences. Further screening with three tPA oligomers corresponding to nucleotides 76 to 95; 1129 to 1148 and 1174 to 1793, respectively, which correspond to the 5', central and 3' regions of the Pennica cDNA sequence was done. This screening identified two clones, λgtPA8 and λgtPA9 which hybridized with all three probes. The sequence was mapped and found to be in agreement with the published tPA genomic clone, Ny et al., supra. The 5' end of the subject genomic clone contains the complete second exon encoding 26 bp of 5'-untranslated sequence plus at least 30 bp of the preceding intron. All of the remaining tPA sequences up to and including the polyadenylation site are present.

An M13 subclone containing a genomic EcoRI fragment spanning positions 801 to 1273 in the cDNA, but containing 2.6 kb of genomic sequence was characterized in detail by restriction endonuclease mapping and partial DNA sequence analysis. By these analyses, the two EcoRI sites at the ends of the clone were shown to be the two sites which exist in the cDNA. By substituting the genomic EcoRI fragment for the EcoRI fragment of the cDNA, a hybrid gene containing three natural introns would be obtained.

The following procedure was used for the preparation of expression vectors containing the hybrid gene: Plasmid pSV7tPA2 was constructed by excising the full length tPA CDNA from an M13 cloning vector by digestion with HindIII, the overhang filled in by the Klenow fragment of DNA polymerase I and dNTPs, followed by digestion with BalI. The resulting about 2100 bp fragment was gel purified. pSV7b, a pML (Lusky and Botchan, Nature (1981) 293:79-81) based plasmid contains the SV40 origin, early promoter and polyadenylation site and a polylinker including BglII and SmaI sites between the promoter and polyadenylation site. The plasmid was digested with BglII and SmaI, where the BglII site was filled in with DNA polymerase I (Klenow fragment) and dNTPs. The 2100 bp tPA cDNA was ligated to pSV7b, the ligated DNA was transformed into competent $E.$ $coli$ HB101, ampicillin-resistant clones selected and grown, and small-scale DNA preparations screened for the correct insert. Fine Structure restriction mapping confirmed that the tPA cDNA and flanking sequences were not detectably deleted or rearranged. The DNA sequence was also established for the 5' end of the tPA insert. The resulting plasmid is referred to as pSV7tPA2.

pSV7tPA2 was digested with EcoRI, and the 2.6 kb genomic EcoRI fragment spanning cDNA positions 801 to 1273 described above was substituted into the cDNA. The resulting plasmid pSV7tPA2I was isolated and characterized by restriction mapping to establish that the correct structure was present.

2. Assays for tPA

There are two types of assays used for tPA, both described by Granelli-Piperno and Reich, (1978) $J.$ $Exp.$ $Med.$ 148:223-234. The first of these is used to assay live cells directly using a casein-agar-plasminogen overlay. When used on COS cells or CHO cells, the assay allows identification of cells which have been transfected with the tPA expression plasmid and which are expressing the gene at a level detected by the assay. Since the transfection efficiencies of the two types of cells are documented and constant (5%-15% for COS Cells and $1 \times 10^{-4}$ per μg for CHO cells), the assay measures the relative expression efficiency of different constructions. The results are seen as a difference in number and size of the cleared zones over the cells expressing tPA.

Agar overlays containing milk, plasminogen, and nutrient medium without serum are prepared as follows (per 6 cm dish):
 0.2 ml 2.5% Difco agar
 0.125 ml 8% milk (boiled 30 minutes in $H_2O$ bath)
 0.25 ml DMEM or 0.25 ml of 2-fold concentrated (2x) DMEM
 0.025 ml 7.5 U/ml plasminogen, sterile filtered Components are mixed in order at 45° C.-50° C. and pipetted onto cells (from which media has been aspirated). Cells are monitored for the production of tPA by inspecting for clear spots in the cloudy overlay. Photographs are taken after 2-6 hours of incubation at 37° C. COS cell assays are recorded by photography and counting of cleared zones; CHO cells are scored for number of cleared zones and individual clones are picked for expansion directly from the assay plate to microwell plates.

The second version of the assay is quantitative and is used to measure the tPA production per cell of permanent expressor lines of CHO cells. Supernatants are removed from cultures of producing cells after 24 or 48 hours of incubation, and cells are removed by trypsinization and counting in a hemacytometer. The supernatants are used undiluted or diluted and are applied to holes punched in casein-agarose-plasminogen lates. The size of the radial zone of clearing is proportional to the concentration of tPA in the sample.

Casegn-plasminogen-agarose plates are prepared by mixing 4.25 ml agarose (3.5%), 6.2 ml 2x DMEM with no added serum, 3.75 ml milk (8% nonfat dry milk powder in water, heated 30 min. in boiling water bath), and 0.2 ml plasminogen (7.5 U per ml) at 48° C. and pipetting the mixture onto glass plates to achieve a gel of uniform thickness and smooth surface. After cooling for approximately 5 minutes to harden, holes are punched into the agar at regular intervals using a metal punch, and the holes are removed by aspiration. Plates thus prepared are stored in a humid atmosphere at 4° unyil use (within 8 hours). Samples are applied using a Pipetteman, 5 microliters per well. The urokinase stock (1700 IU per vial) is dissolved in 340 microliters of distilled water or PBS to a final concentration of 5,000 IU per ml. This stock is diluted in PBS or DMEM (no difference in these buffers) by adding 4 μl of the stock (5,000 IU per ml) to 16 μl of diluent (1/5 dilution). Ten μl of the 1/5 stock is added to 90 μl of diluent for a 1/50 dilution. Fifty μl of the 1/50 dilution is added to 50 μl of diluent for the 1/100 dilution, and all subsequent 2-fold dilutions are done in this manner. Dilutions of urokinase are prepared fresh each day from the stock, which is stored at 4° C. in PBS. Standard solutions are monitored for loss of activity by comparison at two week intervals to freshly dissolved urokinase powder. Test samples are diluted 2-fold in the same diluent as the standard. Plates are incubated at 37° C. in a humid chamber and monitored as a function of time by Polaroid photography. The sizes measured are converted to actual sizes by use of a metric ruler and relating the photograph size to actual size.

3. Transfections and tPA Expression Levels

COS-7 cells (Gluzman, *Cell* (1981) 23:175) were transfected with both plasmids pSV7tPA2 and pSV7tPA2I, using a modification of the procedure described by Graham and van der Eb, *Virology* (1973) 52:456–467. The samples were added to the dishes in duplicate and allowed to settle onto the cells for 6 hr in a $CO_2$ incubator (37° C.). Six hours later the supernatants were aspirated and the cells rinsed gently with calcium- and magnesium-free phosphate-buffered saline (PBS-CMF). The dishes were exposed to qlycerol as an adjuvant for 3.5–4-min, rinsed and fed with DMEM medium, supplemented with 4.5 mg/ml glucose, 3.7 mg/ml sodium bicarbonate, 292 μg/ml glutamine, 110 μg/ml sodium pyruvate, 100 units/ml penicillin, 100 units/ml, streptomycin, and 10% fetal calf serum (FCS). At various times after the adjuvant shock, the medium was replaced with medium lacking fetal calf serum. Twelve hours after serum withdrawal, cells were assayed for expression of tPA using the casein-plasminogen-agar overlay as previously described. Maximum expression was observed between 36 and 48 hr after the start of the transfection.

The number of cleared zones in the dishes transfected by pSV7tPA2I was two to three-fold higher than that with pSV7tPA2 (Table I). Because the transfection frequency is a constant in COS cells, this result signifies better expression in the construction containing the introns. Since the introns were the only differences between the two constructions, the improvement must be attributed to the presence of the introns.

CHO dhfr⁻ cells (Urlaub & Chasin *Proc. Natl. Acad. Sci. USA* (1980) 77:4216) were plated at a density of $5 \times 10^5$ to $10^6$ cells per 10 cm dish the day prior to transfection in nutrient medium (F12 supplemented with 1.18 mg/ml sodium bicarbonate, 292 μg/ml glutamine, 110 μg/ml sodium pyruvate, 100 u/ml penicillin, 100 u/ml streptomycin, 150 μg/ml proline and 10% FCS). The cells were transfected by the same method used to transfect COS cells, except that the tPA expression plasmid (pSV7tPA2 or pSV7tPA2I) was mixed with a plasmid bearing as a selectable marker, a dhfr gene driven by the adenovirus major late promoter, and these plasmids were coprecipitated in calcium phosphate. The plasmid bearing the dhfr gene was constructed by fusing the major late promoter from adenovirus-2 (Ad-MLP, map units 16–17.3) to the mouse dhfr cDNA at the 5' end. DNA coding for the intron for SV40 small t Antigen and the SV40 early region polyadenylation site was obtained from pSV2-neo, described in Southern and Berg, *J. Mol. Appl. Genet.* (1982) 1:327–341, and fused to the 3' end of the dhfr cDNA. These three segments were subcloned into pBR322 to obtain the plasmid Ad-dhfr. This plasmid is functionally similar to the dhfr plasmid described in Kaufman and Sharp, supra. Forty-eight hours after the addition of DNA to the cells, the cells were split 1:20 into selective medium (DMEM supplemented with proline and fetal calf serum as above, or with dialyzed fetal calf serum). After growth in selective medium for 1 to 2 weeks, colonies appeared and were assayed for production of tPA by the casein-plasminogen-agar overlay assay and in casein-agarose-plasminogen plates for quantitation.

Positive clones were more numerous and cleared zones were larger in the plates with cells transfected with pSV7tPA2I than those transfected with pSV7tPA2. Individual clonal lines have been grown up and assayed for production of tPA to compare the expression levels per cell (pg/cell). The results for the lines isolated to date are summarized in Table II.

As shown in Table II, the levels of tPA produced (measured on a per cell basis) are significantly higher in the pSV7tPA2I lines than in the pSV7tPA2 lines. The increase ranges from 1.5 to 16.5-fold.

TABLE 1

Comparison of transient tPA expression using a cDNA containing plasmid (pSV7tPA2) or an intron (pSV7tPA2I).

| DNA | Clear Zones[1] (for molar equivalents of plasmid) | Average |
|---|---|---|
| None | 0 | 0 |
| | 0 | 0 |
| pSV7tPA2 (+) | 460 | 550 |
| | 640 | |
| pSV7tPA2I (+) | 1482 | 1392 |
| | 1302 | |

[1]Transfections were done with 7.5 μg of plasmid per dish. Zones were scored 2 hours after addition of the plasminogen-casein-agar overlay to the plates. Over-lays were done at 36 hours after the adjuvant shock, 42 hours after addition of the DNA to the cells.

TABLE II

Comparison of tPA expression between pSV7tPA2 and pSV7tPA2I clones in CHO cells.[1]

| Line | tPA Level (pg/cell) |
|---|---|
| pSV7tPA2 Derivatives | |
| 9-1 | 0.13 |
| 9-4[1] | <0.27 |
| pSV7tPA2I Derivatives | |
| 7-9 | 3.30 |
| 7-15[1] | 0.36 |
| 7-19[1] | 0.77 |
| 7-21 | 4.35 |
| 7-26 | 2.00 |

[1]Based upon nonconfluent cultures.

It is evident from the above results that remarkable enhancements in production of tPA can be achieved by employing a gene containing at least one and preferably a plurality of introns. Since variable results have been obtained previously in the literature concerning the necessity for introns and these results have been interpreted as the introns contributing to messenger RNA stability, the present result of increased expression and higher efficiencies of productive transfection could not have been predicted from the prior art. The subject invention therefore provides an improved method for making an important mammalian protein, tissue plasminogen activator where higher yields can be obtained so as to allow for higher efficiencies in production and purification and greater economies.

Although the foregoing invention has been described in some detail by way of illustration and example for purposes of clarity of understanding, it will be obvious that certain changes and modifications may be practiced within the scope of the appended claims.

What is claimed is:

1. A DNA construct, comprising:
 a chimeric gene having a coding sequence for human tissue plasminogen activator with at least one intron of at least 100 bp at a site natural to the genomic form of human tissue plasminogen activator gene, wherein said intron includes a 5' splice site and a 3' splice site and provides increased expression of said chimeric gene relative to an uninterrupted coding sequence lacking all introns and wherein said chimeric gene is capable of producing mRNA having the proper reading frame wherein said gene contains fewer than the total number of introns present in the genomic form of the gene for human tissue plasminogen activator, and transcriptional initiation and termination regulatory sequences functional in a mammalian host, at least the initiation sequence being an initiation sequence other than the initiation sequence for the genomic form of the gene for human tissue plasminogen activator.

2. An expression vector capable of stable maintenance in a mammalian host comprising a DNA construct according to claim 1.

3. A mammalian cell in culture containing an expression vector according to claim 2.

4. A mammalian cell in culture wherein DNA construct according to claim 1 is integrated into a chromosome.

5. A DNA construct according to claim 1, wherein each of said introns is natural to human tissue plasminogen activator gene.

6. An expression vector capable of stable maintenance in a mammalian host comprising a DNA construct according to claim 5.

7. A DNA construct according to claim 5, wherein a 2.6 Kb EcoRI-EcoRI fragment from complete digestion with EcoRI of the genomic gene of human tissue plasminogen activator is substituted for an EcoRI-EcoRI region of a cDNA coding for human tissue plasminogen activator.

8. A mammalian cell in culture wherein a DNA construct according to claim 7 is integrated into a chromosome.

9. An expression vector capable of stable maintenance in a mammalian host comprising a DNA construct according to claim 7.

10. A mammalian cell in culture containing an expression vector according to claim 9.

11. A method for producing tissue plasminogen activator in a mammalian cell host comprising:

providing a chimeric gene for human tissue plasminogen activator with at least one intron of at least 100 bp at a site natural to the genomic form of human tissue plasminogen activator gene, wherein said intron includes a 5' splice site and a 3' splice site and provides increased expression of said chimeric gene relative to an uninterrupted coding sequence lacking all introns and wherein said chimeric gene is capable of producing mRNA having the proper reading frame, wherein said gene contains fewer than the total number of introns present in the genomic form of the gene for human tissue plasminogen activator;

placing said chimeric gene for human tissue plasminogen activator with at least one intron under the transcriptional control of a promoter region other than the promoter region natural to human tissue plasminogen activator gene;

introducing said chimeric gene for human tissue plasminogen activator with at least one intron under control of said promoter region into said mammalian cell host;

culturing said mammalian cell host; and expressing said chimeric gene for human tissue plasminogen activator with at lest one intron in said mammalian cell host.

12. A method according to claim 11, wherein said chimeric gene comprises cDNA and genomic DNA having at least one intron.

13. A DNA construct according to claim 12, wherein a 2.6 Kb EcoRI-EcoRI fragment from complete digestion with EcoRI of the genomic gene of human tissue plasminogen activator is substituted for an EcoRI-EcoRI region of a cDNA coding for human tissue plasminogen activator.

14. A method according to claim 4, wherein the introns are natural to human tissue plasminogen activator gene.

15. A method according claim 14, having a viral promoter region for regulating transcription of said gene.

* * * * *